(12) United States Patent
Nagasaki et al.

(10) Patent No.: US 6,544,928 B2
(45) Date of Patent: Apr. 8, 2003

(54) VIRUS CAPABLE OF SPECIFICALLY INFECTING, GROWING WITHIN, AND LYSING RED TIDE PLANKTON; A METHOD AND AN AGENT FOR PREVENTING RED TIDE USING THE VIRUS; A METHOD FOR ISOLATING THE VIRUS; AND A METHOD FOR SUBCULTURING THE VIRUS

(75) Inventors: Keizo Nagasaki, Hiroshima (JP); Mineo Yamaguchi, Hiroshima (JP); Shigeru Itakura, Hiroshima (JP); Kenji Tarutani, Hiroshima (JP)

(73) Assignee: Director General of National Research Institute of Fisheries and Environment of Inland Sea, Hiroshima (JP)

( * ) Notice: Subject to any disclaimer, the term of this patent is extended or adjusted under 35 U.S.C. 154(b) by 0 days.

(21) Appl. No.: 09/789,611

(22) Filed: Feb. 22, 2001

(65) Prior Publication Data

US 2001/0025011 A1 Sep. 27, 2001

(30) Foreign Application Priority Data

Feb. 24, 2000 (JP) ......................................... 2000-047958

(51) Int. Cl.$^7$ .......................... A01N 59/00; A01N 63/00
(52) U.S. Cl. ....................................... 504/117; 504/150
(58) Field of Search ....................... 424/204.1; 504/117, 504/150

(56) References Cited

PUBLICATIONS

Nagasaki et al. Applied and Environmental Microbiology, Mar. 1999, vol. 65, No. 3, pp. 898–902, 1999.*
K. Nagasaki et al., Marine Biology 119: 307–312 1994.*
L. Chen et al., "Bonnemaisonia Hamifera Hariot in Nature and In Culture," J. Phycol. 5:211–220 (1969).
K. Nagasaki et al., "Virus–like Particles in Heterosigma akashiwo (Raphidophyceae); a Possible Red Tide Disintegration Mechanism," Marine Biology 119:307–312 (1994).
K. Nagasaki et al., "Viral Mortality in the Final Stage of Heterosigma akashiwo, (Raphidophyceae) Red Tide," Journal of Plankton Research 16:1595–1599 (1994).
K. Nagasaki et al., "Viral Infection in Heterosigma akashiwo (Raphidoophyceae); a Possible Termination Mechanism of the Noxious Red Tide" In Harmful Marine Algal Blooms, pp. 639–644 (Lassus, P., Arzul, G., Erard, E., Gentien, P., Marcaillou, C., eds., Lavoisier Intercept Ltd.) (1995).
K. Nagasaki et al., "The Disintegration Process of a Heterosigma akashiwo (Raphidophyceae) Red Tide in Northern Hiroshima Bay, Japan During the Summer of 1994" In Harmful and Toxic Algal Blooms, pp. 251–254 (Yasumoto, T., Oshima, Y., Fukuyo, Y., eds., Intergovernmental Oceanographic Commission of UNESCO) (1996).

K. Nagasaki et al., "Isolation of a Virus Infectious to the Harmful Bloom Causing Microalga, Heterosigma akashiwo," Aquatic Microbial Ecology 13:135–140 (1997).
K. Nagasaki et al., "Intra–species Host Specificity of HaV (Heterosigma akashiwo virus) Clones," Aquatic Microbial Ecology 14:109–112 (1998).
K. Nagasaki et al., "Effect of Temperature on the Algicidal Activity and Stability of HaV Heterosigma akashiwo virus)," Aquatic Microbial Ecology 15:211–216 (1998).
K. Nagasaki et al., "Growth Characteristics of Heterosigma akashiwo Virus and Its Possible Use as a Microbiological Agent for Red Tide Control," Applied and Environmental Microbiology 65:898–902 (1999).
K. Nagasaki et al., "Cryopreservation of a Virus (HaV) Infecting a Harmful Bloom Causing Microalga, Heterosigma akashiwo (Raphidophyceae)," Fisheries Science 65:319–320 (1999).
K. Nagasaki et al., "Cluster–Analysis on Algicidal Activity of HaV Clones and Virus Sensitivity of Heterosigma akashiwo, (Raphidophyceae)," Journal of Plankton Research 21:2219–2226 (1999).
K. Nagasaki, "Mortalitiy of Heterosigma akashiwo by viral lysis," In Prevention and Control of Red Tide Microalgae by Microorganisms, pp. 110–119 (Ishida, Y. and Sugahara, I., eds., Koseisya–Koseikaku) (1994).
K. Nagasaki, "Possible Use of Viruses as Microbial Agents Against Heterosigma akashiwo Red Tides," Aqua Culture Magazine 31:126–127 (1995).

(List continued on next page.)

Primary Examiner—Laurie Scheiner
(74) Attorney, Agent, or Firm—Finnegan, Henderson, Farabow, Garrett & Dunner, L.L.P.

(57) ABSTRACT

The present invention provides a virus capable of specifically infecting and growing within a member of algae Heterocapsa sp. A method for isolating the above virus comprises a process of: filtrating with a filter a liquid sample containing a member of algae Heterocapsa sp. infected with a virus capable of specifically infecting and growing within said Heterocapsa sp.; inoculating the obtained filtrate into a culture solution of a member of algae Heterocapsa sp. and culturing; and cloning the above virus by performing a limiting dilution for a culture solution wherein said Heterocapsa sp. is observed to be lysed. The present invention provides an agent for preventing red tide, which comprises, as an active ingredient, the above virus. Furthermore, the present invention provides a method for preventing red tide, which comprises dispersing the above virus in red tide fouled-waters. A method for subculturing the above virus comprises a process repeating at least once of: centrifuging a culture solution of a member of algae Heterocapsa sp., wherein cell lysis is observed as a result of infection with a virus capable of specifically infecting and growing within said Heterocapsa sp. and; inoculating the obtained supernatant into a culture solution of a member of algae Heterocapsa sp.; and culturing.

8 Claims, 3 Drawing Sheets

OTHER PUBLICATIONS

K. Nagasaki, "Mortality of Heterosigma akashiwo Red Tides by Viral Lysis," *BRAIN Techno News* 51:4–7 (1995).
K. Nagasaki, "Viral Ecology in Aquatic Systems," *Journal of the Japanese Society for Marine Biotechnology* 8:16–27 (1995).
K. Nagasaki et al., "Prevention and Control of Red Tide by Viral Lysis," Gyosei–no–Mado 330:2–4 (1997).
K. Nagasaki, "Prevention of Red Tide by Viral Lysis," Umiushi–tushin 17:2–4 (1997).
K. Nagasaki, "Elimination of Harmful Algal Blooms by Viral Algicidity,"*Techno Innovation* 7(28):22–27 (1997).
K. Nagasaki, "Turning the Tide," *World Water and Environment Engineering* 21:18, 20 (1998).
K. Nagasaki, "Possible Use of Algicidal Viruses as Microbial Agents Against Harmful Algal Blooms," *Microbes and Environments* 13:109–113 (1998).
K. Nagasaki, "A Virus that can Eliminate a Harmful Algal Bloom," *Bioscience and Industry* 56:39–40 (1998).
M. Yamaguchi et al., "Overview on Red Tide Outbreaks and Their Countermeasures in Japan," *Proceedings of Techno–ocean '98 International Symposium*, pp. 37–40 (1998).
K. Nagasaki et al., "Simultaneous Extinction of a Heterosigma akashiwo Red Tide," *Research Journal of Food and Agriculture* 22:38–43 (1999).
K. Nagasaki et al., "Studies on the Virus Infecting the Harmful Bloom Forming Microalga *Heterosigma akashiwo*–1. Detection of Viral Infection," *Abstracts for the Meeting of the Japanese Society of Fisheries Science*, p. 86 (Apr. 1993).
K. Nagasaki, "Mortality of *Hetersigma akashiwo* by Viral Lysis, " *Abstracts for the Meeting of the Japanese Society of Fisheries Science*, p. 313 (Apr. 1993).
K. Tarutani et al., "Studies on the Virus Infecting the Harmful Bloom Forming Microalga *Heterosigma akashiwo*–XVII. Comparison Between Viral Susceptibility and Immunological Characteristics of *H. akashiwo* Cells," *Abstracts for the Meeting of the Japanese Society of Fisheries Science*, p. 98 (1999).
K. Nagasaki et al., "Studies on the Virus Infecting the Harmful Bloom Forming Microalga *Heterosigma akashiwo*–XVIII. Designs of DNA Primer Sets Specific to HaV," *Abstracts for the 15th Meeting of the Japanese Society of Microbial Ecology*, p. 17 (1999).
K. Nagasaki et al., "Viral Impact of Harmful Algal Blooms (HABs): Possible Control of HABs by Use of Viruses," *Abstracts of the United State–Japan Cooperative Program on Development & Utilization of Natural Resources–Joint Panel on Toxic Microorganisms*. (no date or page given).
K. Nagasaki et al., "Possible Use of Algicidal Viruses as Microbial Agents Against Harmful Algal Blooms," *Abstracts for the 9th Workshop on the Natural Enemy*, p. 19 (1999).
J. Tyrrell et al., "Phylogeny of the Raphidophytes *Heterosigma carterae* and *Chattonella antiqua* Using 'V4' Domain SSU rDNA Sequences," *Biochem. System. and Ecol.* 24:221–235 (1996).
Y. Hara et al., "Morphology, Ultrastructure, and Taxonomy of the Raphidophycean Alga," *The Botanican Magazine*, 100:151–163 (1987).
T. Horiguchi, "*Heterocapsa circularisquama* sp. nov. (Peridiniales Dinophyceael): A new Marine Dinoflagellate Causing Mass Morality of Bivalves in Japan," *Phycol. Res.* 43:129–136 (1995).

Y. Matsuyama, "Harmful Effect of Dinoflagellate *Heterocapsa circulasrisquama* on Shellfish Aquaculture in Japan," *JARQ* 33:283–293 (1999).
K. Nagasaki et al., "Studies on the Virus Infecting the Harmful Bloom Forming Microalga *Heterosigma akashiwo*–VIII. Cryopreservation of HaV," *Abstracts for the Meeting of the Japanese Society of Fisheries Science*, p. 136 (Apr., 1998).
K. Tarutani et al., "Studies on the Virus Infecting the Harmful Bloom Forming Microalga *Heterosigma akashiwo*–IX. Cluster–analysis in Algicidal Activity of HaV Clones and Virus Sensitivity of *H. akashiwo*," *Abstracts for the Meeting of the Japanese Society of Fisheries Science*, p. 136 (1998).
K. Nagasaki et al., "Prevention and Control of Red Tide by Viral Lysis," *Abstracts for the 2nd Meeting of the Japanese Society of Marine Biotechnology*, p. 53 (1998).
K. Nagasaki et al., "Prevention of Red Tide by Viral Lysis," *Reports for the Workshop on the Water Management in Enclosed Water*, pp. 21–25 (1998).
K. Nagasaki et al., "Is Red Tide Disintegration Regulated by Viral Algicidity?" *Abstracts for the 1st Algal Virus Workshop*, p. 17 (1998).
K. Nagasaki et al., "Studies on the Virus Infecting the Harmful Bloom Forming Microalga *Heterosigma akashiwo*–X. Dynamics of HaV in the Final Stage of H. akashiwo Red Tide," *Abstracts for the Meeting of the Japanese Society of Fisheries Science*, p. 119 (1998).
K. Nagasaki et al., "Studies on the Virus Infecting the Harmful Bloom Forming Microalga *Heterosigma akashiwo*–XI. Isolation Methods of Algal Viruses," *Abstracts for the Meeting of the Japanese Society of Fisheries Science*, p. 119 (1998).
K. Nagasaki et al., "Studies on the Virus Infecting the Harmful Bloom Forming Microalga *Heterosigma akashiwo*–XII. Algicidal Effects of HaV in the Mixed Algal Culture and Natural Seawater Culture," *Abstracts for the Meeting of the Japanese Society of Fisheries Science*, p. 119 (1998).
K. Nagasaki et al., "Studies on the Virus Infecting the Harmful Bloom Forming Microalga *Heterosigma akashiwo*–XIII. Intra–species Diversity of Viral Sensitivity Of H. akashiwo Cells in Natural Seawater," *Abstracts for the 15th Meeting of the Japanese Society of Microbial Ecology*, p. 65 (1998).
K. Nagasaki et al., "Interactions Between Virus and Its Host Algae During the Final Stage of Red Tides," *Abstracts for the Symposium of the Japanese Society of Microbial Ecology*, p. 146 (1998).
K. Nagasaki et al., "Studies on the Virus Infecting the Harmful Bloom Forming Microalga *Heterosigma akashiwo*–XIV. Interactions Between *H. Akashiwo* and HaV in Natural Environments," *Abstracts for the Meeting of the Japanese Society of Fisheries Science*, p. 44 (1999).
K. Tarutani et al., "Studies on the Virus Infecting the Harmful Bloom Forming Microalga *Heterosigma akashiwo*–XV. Viral Adsorption to *H. akashiwo* Cells," *Abstracts for the Meeting of the Japanese Society of Fisheries Science*, p. 44 (1999).
K. Nagasaki et al., "Studies on the Virus Infecting the Harmful Bloom Forming Microalga *Heterosigma akashiwo*–XVI. Genetic Analysis of HaV–1," *Abstracts for the Meeting of the Japanese Society of Fisheries Science*, p. 98 (1999).

K. Nagasaki et al., "Studies on the Virus Infecting the Harmful Bloom Forming Microalga *Heterosigma akashiwo*–II. Daily Changes of Viral Infection Against *H. akashiwo* in Natural Environments," *Abstracts for the 9th Meeting of the Japanese Society of Microbial Ecology*, p. 61, (1993).

M. Yamaguchi et al., "Studies on the Virus Infecting the Harmful Bloom Forming Microalga *Heterosigma akashiwo*–III. Isolation of *Heterosigma akashiwo* virus from natural seawater," *Abstracts for the Meeting of the Japanese Society of Fisheries Science*, p. 150 (1997).

K. Nagasaki et al., "Studies on the Virus Infecting the Harmful Bloom Forming Microalga *Heterosigma Akashiwo*–IV. Mortality of *Heterosigma akashiwo* by Viral Infection Under Culture Conditions," Abstracts for the Meeting of the Japanese Society of Fisheries Science, p. 150 (1997).

K. Nagasaki et al., "Studies on the Virus Infecting the Harmful Bloom Forming Microalga *Heterosigma akashiwo*–V. Intra–species Host Specificity of HaV Clones," *Abstracts for the 13th Meeting of the Japanese Society of Microbial Ecology*, p. 114 (1997).

K. Nagasaki et al., "Studies on the Virus Infecting the Harmful Bloom Forming Microalga *Heterosigma akashiwo*–VI. Effect of Temperature on the Algicidal Activity of HaV," *Abstracts for the Meeting of the Japanese Society of Fisheries Science*, p. 101 (1997).

K. Nagasaki et al., "Studies on the Virus Infecting the Harmful Bloom Forming Microalga *Heterosigma akashiwo*–VII. Electron Microscopic Observation of HaV Growth Process," *Abstracts for the Meeting of the Japanese Society of Fisheries Science*, p. 101 (1997).

* cited by examiner

→: Inoculation of virus

●: Culture to which the supernatant of lysed culture solution is added

○: Culture to which either less than 0.1 μm of fraction or heat-processed lysed culture solution is added FIG. 3A 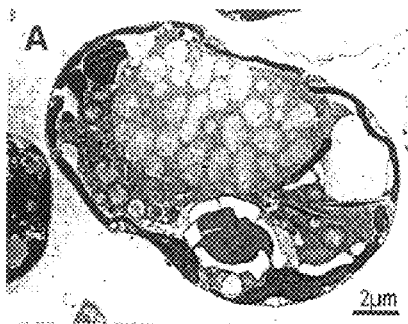 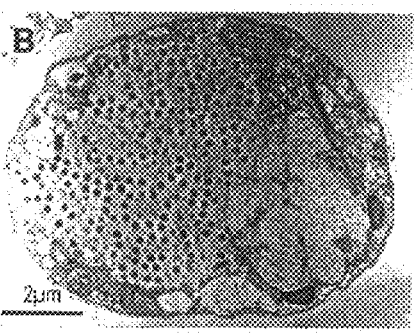 FIG. 3B
FIG. 3C 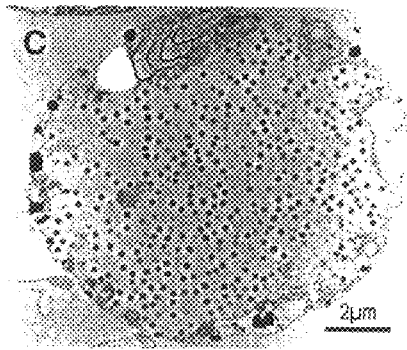 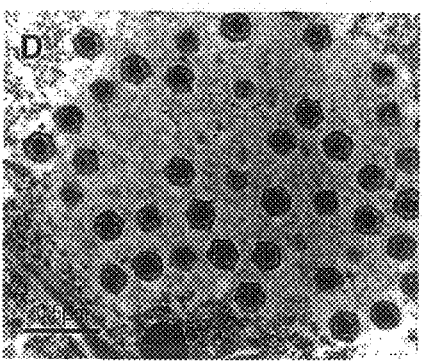 FIG. 3D

VIRUS CAPABLE OF SPECIFICALLY INFECTING, GROWING WITHIN, AND LYSING RED TIDE PLANKTON; A METHOD AND AN AGENT FOR PREVENTING RED TIDE USING THE VIRUS; A METHOD FOR ISOLATING THE VIRUS; AND A METHOD FOR SUBCULTURING THE VIRUS

FIELD OF THE INVENTION

The present invention relates to a virus capable of specifically infecting and growing within red tide plankton; a method and an agent for preventing red tide using the virus; and a method for isolating the virus and a method for subculturing the virus. More specifically, the present invention relates to a virus capable of specifically infecting and growing within a member of algae Heterocapsa sp., a method and an agent for preventing red tide using the virus; and a method for isolating the virus and a method for subculturing the virus.

BACKGROUND OF THE INVENTION

In Japan, the yield from sea surface culture makes up approximately one quarter of the whole yield of the national fishery industry. To promote the sea surface culture, the environmental protection of culture fisheries is indispensable, and above all, it is extremely important to take effective countermeasures against red tide causing severe damage to commercial fisheries.

A red tide-causing alga, Heterocapsa circularisquama, which appeared in Japan in the late 80s, is a kind of dinoflagellate having the property of specifically killing bivalves such as oysters, short-necked clams and pearl oysters, and results in severe financial losses to the bivalve-culture industries of many regions in Japan. In 1998, losses to the culture oyster industry in Hiroshima Bay alone reached approx. 3.8 billion yen. In 1988, when Heterocapsa red tide was recorded for the first time in the world, Heterocapsa cells were observed only in Uranouchi Bay located in Kochi prefecture. However, since then the distribution area of Heterocapsa has rapidly expanded, and at present it is widely distributed throughout the coastal regions of western Japan from Kumamoto prefecture to Fukui prefecture. Fortunately, the movement of this species to neighboring countries has not been reported yet, but the international transport of hazardous and toxic plankton by means of the ballast water of freighters is known, and so the monitoring system of the distribution dynamics of this species needs to be improved.

Against this backdrop, municipalities in each region in Japan strongly desire establishment of concrete measures against Heterocapsa red tide. At this stage, however, there are no concrete measures apart from "the displacement of culture farms". However, the displacement of culture farms from red tide emerging areas is replete with potential danger that Heterocapsa cells are also displaced. Therefore, culturists are required to displace their culture farms with extra care.

SUMMARY OF THE INVENTION

Aiming at the development of practical techniques for preventing Heterocapsa red tide, the present invention is mainly directed to the search for possible applications of a novel isolated virus, Heterocapsa circularisquama Virus (HcV) to prevent red tide. The prevention of red tide by utilizing the virus is expected to be especially useful, and is highly regarded as an environmental protection technique, which is safe and reduces burdens on other living things or on the whole ecosystem. So, if some challenges, e.g. development of mass culture technique and dispersion method of the virus, and achievement of low cost, are resolved, a technique using this virus is expected to proceed toward commercialization in the future.

After performing thorough studies to overcome the above-stated problems, the present inventors have succeeded in isolating for the first time in the world a virus which infects and kills Heterocaspa circularisquama, thereby completing the present invention.

That is to say, the present invention provides a virus capable of specifically infecting and growing within a member of algae Heterocapsa sp. This Heterocapsa sp. can be Heterocapsa circularisquama. In one aspect of the present invention, the virus lacks a tail and an adventitia, adopts a sphere-like regular icosahedral structure with a particle size of approx. 0.1 to 0.2 µm, and has double-stranded DNA.

In addition, the present invention provides a method for isolating a virus capable of specifically infecting and growing within a member of algae Heterocapsa sp., which comprises a process of: filtrating with a filter a liquid sample containing a member of algae Heterocapsa sp. infected with a virus capable of specifically infecting and growing within the above Heterocapsa sp.; inoculating the obtained filtrate into a culture solution of a member of algae Heterocapsa sp. and culturing; and cloning the virus by performing a limiting dilution on a culture solution wherein the above Heterocapsa sp. is observed to be lysed. The pore size of the filter used may be large enough to trap living things larger than bacteria or viruses such as phytoplankton, and for isolating HcV for example, the pore size of filters used may be 0.4 or 0.2 µm. Regardless of whether a member of algae Heterocapsa sp. is cultured before or after infection with the virus of the present invention, the culture is preferably performed at a temperature of 20 to 30° C., photon density of 40 to 70 µmol photons $m^{-2}$ $s^{-1}$, and under a light-dark cycle. Furthermore, the culture may be performed in modified SWM3 medium. As preferable culture conditions, temperature is 20° C., photon density is 45 µmol photons $m^{-2}$ $s^{-1}$, and the light-dark cycle is a 12-hour cycle. Limiting dilution performed during a process of cloning the virus of the present invention may be carried out in a series of $10^{-1}$ to $10^{-7}$ times dilution steps.

Moreover, the present invention provides an agent for preventing red tide, which comprises, as an active ingredient, a virus capable of specifically infecting and growing within a member of algae Heterocapsa sp.

Furthermore, the present invention provides a method for preventing red tide, which comprises dispersing a virus capable of specifically infecting and growing within a member of algae Heterocapsa sp. in red tide-fouled waters.

In addition, the present invention provides a method for subculturing a virus capable of specifically infecting and growing within a member of algae Heterocapsa sp., which comprises a process of repeating at least once the following steps: centrifuging the culture solution of a member of algae Heterocapsa sp., wherein cell lysis is observed as a result of infection with a virus capable of specifically infecting and growing within the above Heterocapsa sp.; inoculating the obtained supernatant into a culture solution of a member of algae Heterocapsa sp.; and culturing. Regardless of whether a member of algae Heterocapsa sp. is cultured before or after infection with the virus of the present invention, the culture thereof is preferably performed at a temperature of 20 to 30°

C., photon density of 40 to 70 μmol photons m$^{-2}$ s$^{-1}$, and under a light-dark cycle. Furthermore, the culture may be performed in modified SWM3 medium. As preferable culture conditions, temperature is 20° C., photon density is 45 μmol photons m$^{-2}$ s$^{-1}$, and the light and dark cycle is a 12-hour cycle.

Throughout the present specification, "red tide" means the development of discoloration of sea water caused by plankton during drastic population increases. This word is widely used, regardless of whether there is damage to aquatic living things presents or not. Representative examples of plankton causing harmful red tide in Japan include Chattonella sp., Gymnodinium sp., Heterosigma sp., etc.

"A member of algae Heterocapsa sp." belongs to Dinophyceae, and among them, species known to belong to Heterocapsa sp. include *Heterocapsa circularisquama, Heterocapsa triquetra, Heterocapsa illdefina*, etc.

"*Heterocapsa circularisquama*" is a relatively small dinoflagellate (approx. 20 μm in dimension) having the property of specifically killing shellfish, while not affecting other Pisces. In 1988, red tide caused by this species occurred for the first time in Uranouchi Bay located in Kochi prefecture, and it resulted in severe losses, killing 1,500 tons of short-necked clams. Since then, red tides caused by this species have expanded throughout western Japan, and severe damage to the fishery industry occurs almost every year. Since the toxicity of this species to shellfish is specific and lethal, there is a possibility that an unknown mechanism of the species causes the death of shellfish. For this reason, even now several thorough studies are being conducted in order to clarify the mechanism of the toxicity of this species.

"Virus" means a spherical or fibrous microstructure capable of growing only within a host cell infected with the same. Viruses are completely different from bacteria in that it is incapable of growing by binary fission, but capable of self-replicating only by utilizing the biosynthetic system of a host cell. When compared with bacteria, viruses are characterized by having significantly high host specificity. "Host specificity" is an expression indicating the limitation of types of host organisms which pathogenic parasites (which are viruses herein) are able to infect and grow within. For instance, an expression such as to "have high host specificity" or to "have narrow host range" means that there are a few kinds of organisms which parasites are able to infect.

BRIEF DESCRIPTION OF THE DRAWINGS

FIGS. 3A–3D shows the photographs of each Heterocapsa cell (Heterocapsa Hu9433 (-) strain) infected or not infected with HcV01, taken by a transmission electron microscope at the following stages 3A to 3D.

Figure 1:
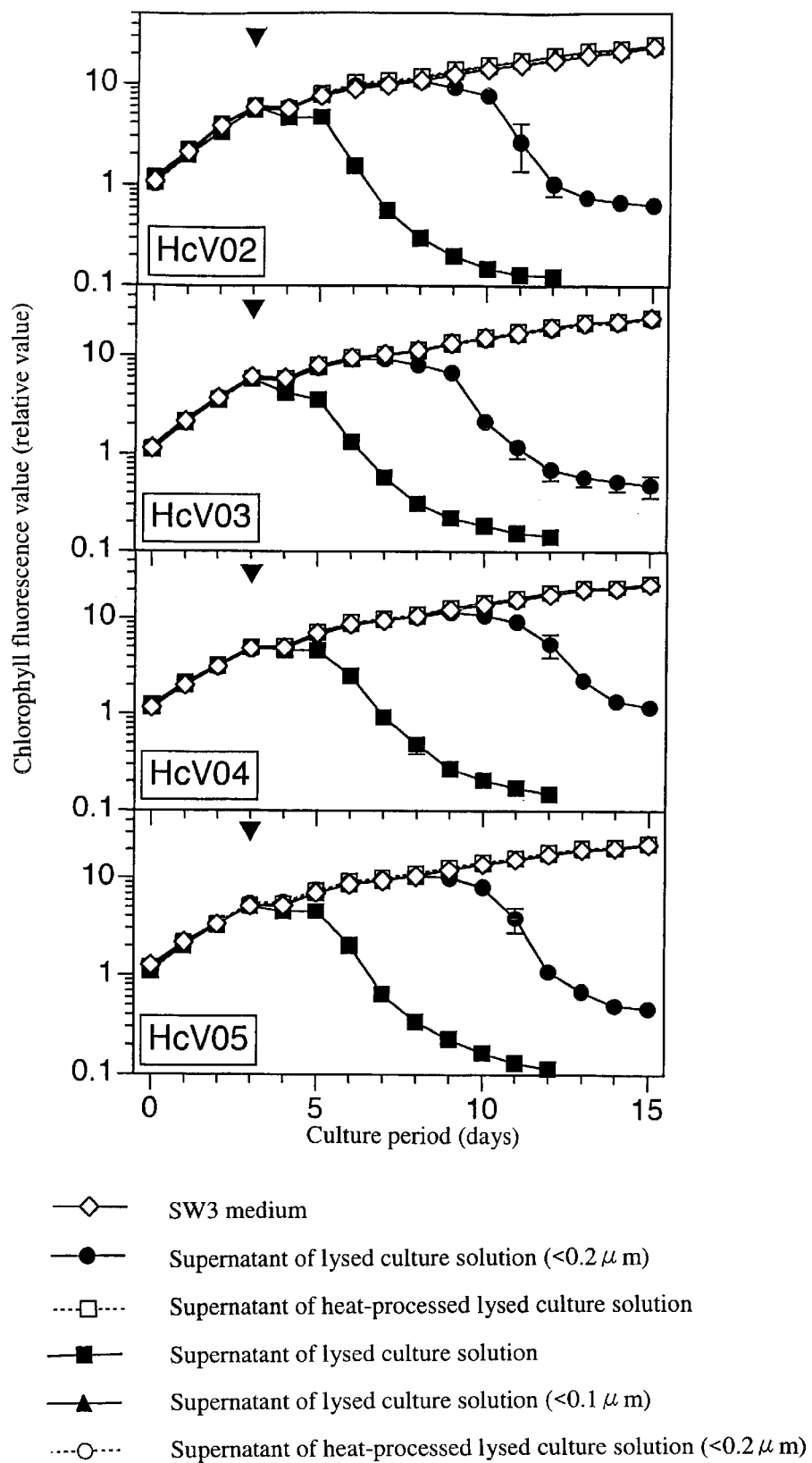
FIG. 1 shows the growth of a Heterocapsa Hu9433 (-) strain, into which an algicidal factor clone given various pretreatments was inoculated.

3A: A healthy Heterocapsa cell (Heterocapsa Hu9433 (-) strain).

3B: A Heterocapsa cell at 48 hours after infection with the virus. Pores appeared on some parts of nuclear membrane, and a large number of viral particles were produced within a viroplasm composed of intranuclear substances leaking into the cytoplasm.

3C: A Heterocapsa cell entirely infected with the virus. The nucleus of the host disappeared.

3D: An enlarged image of the virus growing within Heterocapsa cell. From the fact that the cross section forms a pentagon or a hexagon, it is clear that this virus adopts stereoscopically a regular icosahedral structure. Particle size is approx. 200 nm.

DETAILED DESCRIPTION OF THE INVENTION

The present invention is described in detail below.

The object organism of the present study *Heterocapsa circularisquama* is a red tide-causing alga that appeared in Japan in the late 80s, and it is a kind of dinoflagellate having the property of specifically killing bivalves such as oysters, short-necked clams and pearl oysters, thus resulting in severe financial losses to the bivalve-culture industries of many regions in Japan.

The virus of the present invention is capable of specifically infecting and growing within a member of algae Heterocapsa sp. *Heterocapsa circularisquama* Virus (HcV), which is capable of infecting and growing within *Heterocapsa circularisquama*, lacks a tail and an adventitia, adopts a sphere-like regular icosahedral structure with a particle size of approx. 0.15 to 0.25 μm, and has double-stranded DNA. Under experimental circumstances, Heterocapsa cells infected with this virus lose their mobility and die. At this moment, the virus releases a large number of replicated apomorphic viruses, inducing the infection and death of new (and uninfected) Heterocapsa cells. Thus, only by the addition of a single virus into a medium containing several millions to several ten millions of *Heterocapsa circularisquama* cells, it is possible to completely kill all the cells contained in the medium. Furthermore, since the present virus has high host specificity, no influence on phytoplankton other than *Heterocapsa circularisquama* has been detected up till now.

The virus of the present invention can be isolated as follows. A sea water sample containing a member of algae Heterocapsa sp. infected with a virus capable of specifically infecting and growing with the algae Heterocapsa sp. (e.g. sea water collected at the late stage of red tide) is prepared and conserved at approx. 4° C. This Heterocapsa sp. is preferably *Heterocapsa circularisquama*. After the water sample is filtrated through filters whose pore sizes are 0.4 μm and 0.2 μm, the obtained filtrate is inoculated into a culture medium of a member of algae Heterocapsa sp., and the mixture cultured under the conditions: e.g. 20° C., 45 μmol photons m$^{-2}$s$^{-1}$, a cycle of 12 hours each in light and dark. The culture solution of a member of algae Heterocapsa sp. can be prepared by previously cloning the alga by: micropipet method or limiting dilution to establish cell lines, inoculating into modified SWM3 medium containing 2 nM Na$_2$SeO$_3$ (Chen et al., 1969, *J. Phycol* 5:211–220; Itoh & Imai, 1987, Shuwa, Tokyo, p.122–130), and then culturing the mixture at 20° C. while irradiating with a 45 μmol photons m$^{-2}$s$^{-1}$ white fluorescent light in a cycle of 12 hours each in light and dark. By culturing under the above conditions, a member of algae Heterocapsa sp. enters the exponential growth phase approx. 2 to 4 days after the initiation of culture, and this period lasts for approx. 10 to 14 days.

Subsequently, the virus is cloned by performing a limiting dilution on the culture solution in modified SWM3 medium, wherein algal lysate of Heterocapsa sp. is observed. The method for preparing the culture solution of Heterocapsa sp. is described as above. A limiting dilution may be carried out as follows. First, the culture solution, wherein algal lysate of Heterocapsa sp. is observed, is diluted with modified SWM3 medium in a series of 10$^{-1}$ to 10$^{-7}$ times dilution steps, and each obtained dilution is inoculated into an exponentially growing culture solution of Heterocapsa sp. Each of these mixtures is cultured for 7 to 10 days under the following conditions: e.g. 20° C., 45 µmol photons $m^{-2}s^{-1}$, a cycle of 12 hours each in light and dark. After culturing, a culture solution with the highest degree of dilution, wherein cell lysis of Heterocapsa sp. is observed, is selected, and the above-stated stepwise dilution of the culture solution is repeated at least once (e.g. twice to three times).

After the final stepwise dilution, among culture solutions wherein cell lysis is observed, a culture solution with the highest degree of dilution is collected, and inoculated into the exponentially growing culture solution of Heterocapsa sp. Thus, clonal viruses of the virus of the present invention can be obtained. Cell residue is removed from the culture solution of Heterocapsa sp. containing clonal viruses by centrifugation (e.g. at 7,000 rpm, for 2 minutes). Then, 4',6'-diamidino-2-phenylindole (hereinafter referred to "DAPI") dissolved in Tris buffer containing cysteamine hydrochloride is added to the obtained supernatant. After staining in the dark, viral particles are captured on a 0.02 µm pore size filter by filtration under reduced pressure, and then a fluorescence microscopy is performed under X-ray excitation.

By dispersing the virus of the present invention in red tide fouled-waters, red tide can be prevented. For preventing red tide, the culture solution or supernatant of the virus of the present invention can be used, but as an option, a formulation containing, as an active ingredient, the virus of the present invention can be prepared and used.

Since the method and agent for preventing red tide according to the present invention use a virus with high host specificity, which exists in the natural environment, these are highly evaluated as safe environmental protection techniques reducing burdens on the ecosystem. Furthermore, the red tide preventing agent of the present invention differs from other general agents in that the virus itself has a self-replicating ability, and so it is expected that only a small amount of the agent can control far-ranging red tides.

A method for subculturing a virus capable of specifically infecting and growing within a member of algae Heterocapsa sp. is described below.

A culture solution of Heterocapsa sp., which is observed to be infected and lysed by a virus capable of specifically infecting and growing within Heterocapsa sp., is centrifuged (e.g. at 7,000 rpm for 2 minutes), the obtained supernatant is inoculated into an exponentially growing culture solution of Heterocapsa sp., and the mixture is cultured. This process is repeated a number of times. Subsequently, the growth of the alga can be evaluated by monitoring in vivo chlorophyll fluorescence using a fluorometer over the course of time. This clarifies that the virus subcultured by the above-stated method retains infectivity against a member of algae Heterocapsa sp.

EXAMPLE

The present invention is further described in the following example. The example is provided for illustrative purposes only, and is not intended to limit the scope of the invention. Unless otherwise specified in the following examples, the % symbol represents volume %.

Example 1.

Material and Method

Plankton sample

To isolate an algicidal factor, Heterocapsa Hu9433(−) strain isolated from water in Uranouchi Bay (Kochi prefecture, Japan) and Heterocapsa HA92-1 strain isolated from water in Ago Bay (Mie prefecture, Japan) were used. Both strains were aseptic clonal strains. Heterocapsa HA92-1 strain is known to have symbiotic bacteria within the cell, but Heterocapsa Hu9433 (−) strain does not. Using modified SWM medium, a culture was performed e.g. at a temperature of 20° C., photon density of 45 µmol photons $m^{-2}s^{-1}$ and under a 12-hour cycle in light-dark.

Isolation of algicidal factor

A sea water sample was collected from surface water in Wakinoura Fishing Port in Fukuoka prefecture at the late stage of Heterocapsa red tide bloom in August, 1999. This sample was filtered through 0.4 µm and 0.2 µm pore size membrane filters (Nuclepore), and 1 ml of each of the obtained filtrates was inoculated into 1 ml of each of culture solutions independently containing Heterocapsa Hu9433(−) strain and Heterocapsa HA92-1 strain. As a control sample, less than 0.2 µm fraction treated at 100° C. for 10 minutes was inoculated in a like manner, and cultured under the above conditions.

For the purpose of cloning an algicidal factor, the following limiting dilution was repeated twice. A culture solution, wherein cell lysis was observed after the above culture, was diluted with modified SWM3 medium in a series of $10^{-1}$ to $10^{-7}$ times dilution steps, and 100 µl of each of the obtained dilutions was inoculated into 150 µl of exponentially growing culture solution of Hu9433(−) strain. Microplates with 96 holes were used for this experiment, and for each dilution step, 8 identical experiments were conducted. As a control sample, only modified SWM3 medium-containing culture solution was applied. These mixtures were cultured for 7 to 10 days under the conditions described above. A plurality of lysed cultures were collected from the most diluted wells in which cell lysis occurred, and the above entire procedure was repeated. 200 µl of lysed culture in the most diluted wells of the second assay was collected and transferred into 1 ml of exponentially growing culture solution of Hu9433 strain. Thus, clonal algicidal factors were obtained.

Transmission electron microscopy

One clone (HcV01) was selected from the obtained clonal algicidal factors, and 2.5 ml of the lysed culture solution was inoculated into 50 ml of exponentially growing culture solution of Hu9433 (−) stain. As a control sample, a lysed culture solution heat-processed at 100° C. for 15 minutes was also inoculated and cultured under the above conditions. Samples were collected immediately, at 24 hours, and at 48 hours after inoculation, and after fixing and embedding in accordance with standard techniques, these samples were observed with a JEOL JEM-1010 transmission electron microscope. The form of algicidal factors contained in lysed culture solution was observed by negative staining.

Fluorescence microscopy

From the lysed culture solution containing clonal algicidal factors, cell residue was removed by centrifugation (at 7,000 rpm, for 2 minutes). Then, DAPI solution (15 µg $ml^{-1}$) dissolved in Tris buffer containing cysteamine hydrochloride was added to 1.2 ml of the obtained supernatant. After staining in the dark for 30 minutes, clonal algicidal factors were captured on a 0.02 µm pore size Anodisk filter (Whatman) by filtration under reduced pressure, and then fluorescence microscopy was performed under X-ray excitation.

Inoculation of clonal algicidal factors

The following processes were carried out for lysed culture solutions containing the above clonal algicidal factors to analyze viral infectivity thereof.

1. Centrifugation at 7,000 rpm for 2 minutes
2. Filtration through a 0.2 µm pore size membrane filter
3. Filtration through a 0.1 µm pore size membrane filter
4. Heat-processing at 100° C. for 15 minutes for a lysed culture solution after step 1.

5. Heat-processing at 100° C. for 15 minutes for a lysed culture solution after step 2.

200 μl of each of the lysed culture solutions obtained as above was inoculated into 4 ml of exponentially growing culture solution of Hu9433(−) strain, and cultured under the above-stated conditions. As a control sample, an equivalent amount of modified SWM3 medium was inoculated in a like manner. The experiment was performed in triplicate for each culture solution of above steps 1 to 5, and the growth of alga was evaluated by monitoring in vivo chlorophyll fluorescence using a fluorometer over the course of time.

Furthermore, for the purpose of analyzing viral continuity, a lysed culture solution was centrifuged at 7,000 rpm for 2 minutes, and 200 μl of the obtained supernatant was inoculated into 4 ml of exponentially growing culture solution of Hu9433(−) strain. This step was repeated 3 times. As a control sample, an equivalent amount of modified SWM3 medium was inoculated in a like manner, and all the culture solutions were cultured under the above-stated conditions. The experiment was performed in triplicate for each culture solution of the above steps 1 to 5, and the growth of alga was evaluated by monitoring in vivo chlorophyll fluorescence using a fluorometer over the course of time.

Analysis of host range

50 μl of the above lysed culture solution was added to 1 ml of each of culture solutions of exponentially growing algae shown in Table 1, and cultured under the above conditions, with the exception that only 6 strains (Alexandrium tamarense, Chattonella verruculosa, Chaetoceros dydimum, Dirylum brighnweihi, Skeletonema costatum and Thalassiosira sp.) were cultured at 15° C. As a control sample, a lysed culture solution heat-processed at 100° C. for 15 minutes was also inoculated. The experiment was performed in duplicate for each culture solution, and the existence of cell lysis was monitored using an optical microscope over the course of time. Stains wherein cell lysis was not observed at 14 days after inoculation were determined not to be the host of the algicidal factor of the present invention.

Results and Discussion

Isolation of algicidal factor

In both Heterocapsa Hu9433(−) strain and Heterocapsa HA92-1 strain, cells were lysed by addition of less than 0.4 μm of and less than 0.2 μm of fractions of sea water sample, and became extinct. In the case where heat-processed sea water sample was added, however, both strains continued to grow.

5 clonal algicidal factors were isolated from lysed culture solution obtained by inoculation of less than 0.2 μm of a fraction (Table 2). After inoculating a suspension containing these algicidal factors into sterility test medium ST10$^{-1}$, no cloudiness was observed, so it was particularly likely that all of the obtained algicidal factors were aseptic.

Microscopic observation using transmission electron and fluorescence microscopes The results of observation by a transmission electron microscope are shown in FIG. 3.

Heterocapsa cells, into which a heat-processed suspension containing algicidal factors was inoculated, were actively motile even at 24 hours and 48 hours after inoculation. According to observation of cell sections by a transmission electron microscope, it was observed that the cells adopt a healthy intercellular structure.

In contrast, Heterocapsa cells into which non-treated algicidal factors were inoculated, as a step leading to cell lysis, first lost motility and were deposited at the bottom of the culture vessel. Then, the deposited cells conglobed, and at 48 hours after inoculation, a portion of the cells was lysed. According to observation by a transmission electron microscope, a large number of virus-like particles were detected in the cells at 24 hours and 48 hours after inoculation. In each of these particles, a spherical core with high electron density was observed, but a tail and an adventitia were not observed. In addition, according to observation by negative staining, the diameter of these particles was estimated to be 197±8 nm (n=30).

Furthermore, according to the observation of a portion of lysed culture solution with a fluorescence microscope, a large number of DAPI stainable particles were detected, which were smaller than bacteria.

Inoculation of clonal algicidal factors

FIG. 1 shows the growth of Heterocapsa Hu9433 (−) strains containing clonal algicidal factors, on which various types of pretreatment were performed. In Heterocapsa Hu9433 (−) culture to which the supernatant of lysed culture solution was added, chlorophyll fluorescence value was decreased from the next day of addition. In the culture to which less than 0.2 μm of fraction was added, chlorophyll fluorescence value was also decreased, albeit that it occurred 4 to 5 days later than in the case where non-treated supernatant was added as above. However, in the cultures to which both less than 0.1 μm of the fraction and heat-processed lysed culture solution were added, chlorophyll fluorescence value was not decreased even 10 days after inoculation. Furthermore, when compared with the case of addition of SWM3 medium alone, there was no significant difference.

Figure 2:
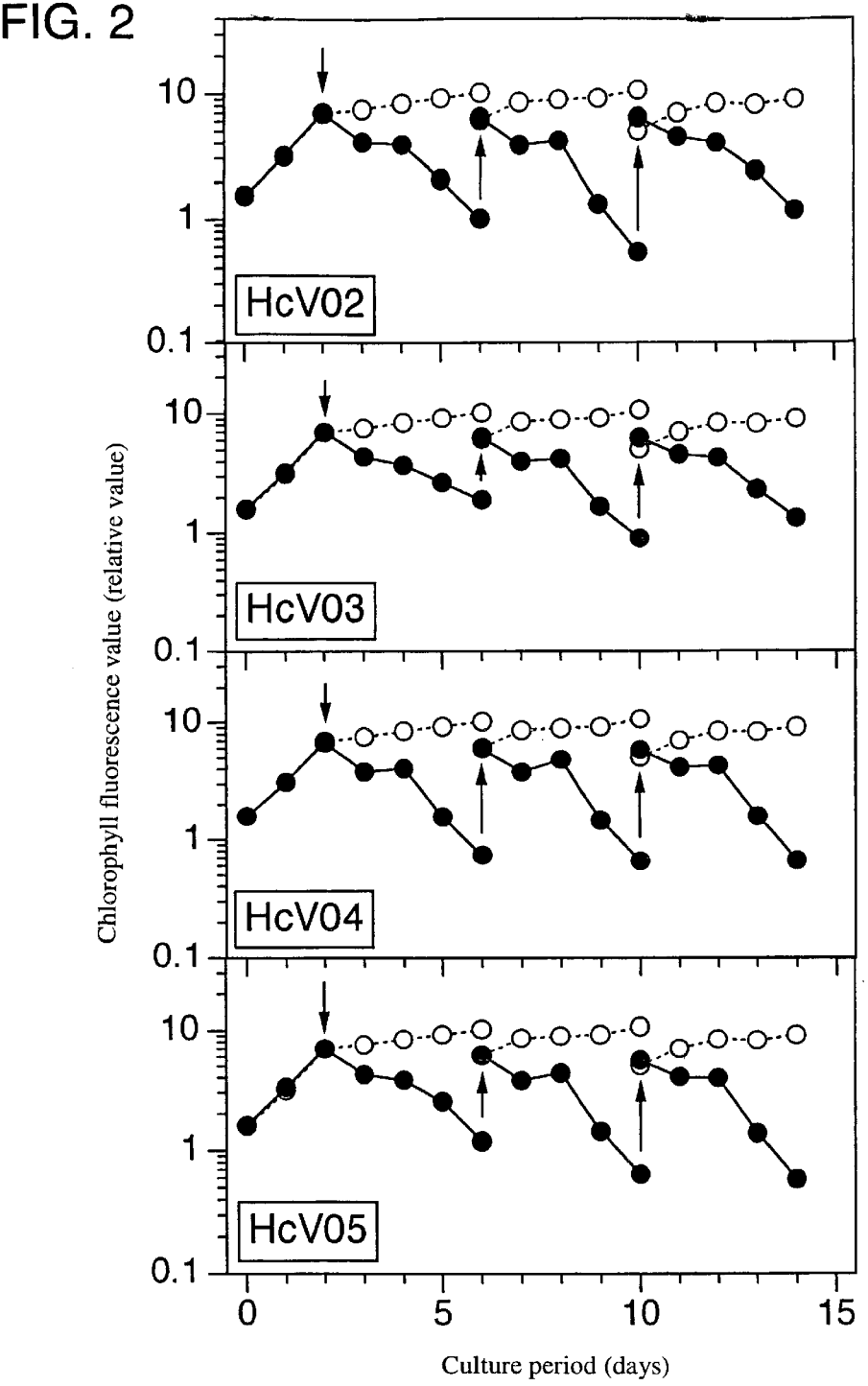
FIG. 2 shows the growth of a Heterocapsa Hu9433 (-) strain, to which an algicidal factor clone was subcultured during the exponential growth phase of the strain.

An experiments regarding serial subculture of the present algicidal factor showed that the clonal algicidal factor of the present invention is able to lyse exponentially growing Heterocapsa cells quickly and repeatedly (FIG. 2).

From the fact that, regarding cell lysis, there is a time lag of some days between the less-than-0.2 μm fraction-added culture and non-treated clonal algicidal factors-added culture, it is assumed that, although some algicidal factors pass through a 0.2 μm filter, a majority of the factors are captured on the filter. From these results, it is suggested that the size of this algicidal factor is approx. 0.2 μm in dimension, and it is thermolabile. This size almost matches to the particle size of virus-like particles detected only in the cells into which algicidal factors were inoculated. Accordingly, this virus-like particle satisfies "Koch law" which consists of the following elements: (1) the bacteria or virus is unfailingly detected in lesional sites, (2) the bacteria or virus is not detected in healthy tissues, (3) the artificial inoculation of the factor can develop a specific disease to a host. Thus, it is clearly shown that this virus-like particle is an algicidal factor that is a virus. Since small particles stainable in DAPI were observed in lysed culture solution, the virus of the present invention was assumed to be a double-stranded DNA virus.

Host specificity

The algicidal factor of the present invention did not show an ability to kill algae against 4 species of Bacillariophyceae, 2 species of Chlorophyceae, 1 species of Cryptophyceae, 9 species of Dinophyceae except some Heterocapsa sp., 1 species of Euglenophyceae, 2 species of Prymnesiophyceae, and 5 species of Raphidophyceae (Table 1). From this result, it is assumed that the virus of the present invention is highly likely to infect Heterocapsa sp. specifically.

TABLE 1

List of phytoplankton strains used for analysis of host range and viral susceptibility of these strains against the clonal algicidal factors of the present invention

| Species (Strain) | Locality | Date | Susceptibity |
|---|---|---|---|
| BACILLARIOPHYCEAE | | | |
| Chaetoceros didymum (Ch-4) | Hiroshima Bay | Mar 1989 | − |
| Ditylum brightwellii (Di) | Hiroshima Bay | Mar 1989 | − |
| Skeletonema costatum (Sk-1) | Hiroshima Bay | Mar 1989 | − |
| Thalassiosira sp. (Th-2) | Hiroshima Bay | Feb 1989 | − |
| CHLOROPHYCEAE | | | |
| Nannochloropsis sp. (SFBB) | unknown | unknown | − |
| Oltomannsielopsis viridis | Osaka Bay | Oct 1993 | − |
| CRYPTOPHYCEAE | | | |
| Rhodomonas ovalis | off Fukushima | Jun 1967 | − |
| DINOPHYCEAE | | | |
| Alexandrium catenella (AcUJm) | Uwajima | (sediments) | − |
| Alexandrium tamarense (KR-6) | Kure Bay | Apr 1998 | − |
| Gymnodinium catenatum (GClax) | Inakushi Bay | Apr 1996 | − |
| Gymnodinium mikimotoi (G303-ax2) | Suo Nada | Jun 1985 | − |
| Gymnodinium sanguinum (GSUR974) | | | − |
| Heterocapsa circularisquama (HA92-1) | Ago Bay | Dec 1992 | + |
| Heterocapsa circularisquama (Hu9433(−)) | Uranouchi Bay | Dec 1994 | + |
| Heterocapsa triquetra (H9104) | Hiroshima Bay | Apr 1991 | − |
| Prorocentrum micans (8304) | Hiroshima Bay | Jul 1983 | − |
| Prorocentrum triestinum (H9109) | Hiroshima Bay | Sep 1991 | − |
| Scripsiella trochoidea (SCKR) | Kure Bay | Apr 1997 | − |
| EUGLENOPHYCEAE | | | |
| Eutreptiella sp. (Eut-ax01) | | | |
| PRYMNESIOPHYCEAE | | | |
| Isochrysis galbana | unknown | unknown | − |
| Pavlova lutheri | unknown | unknown | − |
| RAPHIDOPHYCEAE | | | |
| Chattonella antiqua (HBG-8) | Hiuchi Nada | (sediments) | − |
| Chattonella marina (CmUR976) | Uranouchi Bay | Jun 1997 | − |
| Chattonella verruculosa (M) | Hiroshima Bay | May 1993 | − |
| Fibrocapsa japonica (Fib-1) | Harima Nada | Oct 1985 | − |
| Heterosigma akashiwo (H93616) | Hiroshima Bay | Jun 1993 | − |

Thus, the present inventors have succeeded in isolating a virus capable of specifically infecting and killing a dinoflagellate Heterocapsa circularisquama, which forms red tides in various sea areas in western Japan, resulting in serious damage to bivalve-culture industry. To our knowledge, this was the first example of isolating a virus infecting a dinoflagellate, which is one of main sea microalgae groups. After that, 5 clonal viruses infecting Heterocapsa sp. have been isolated from surface sea water in Fukuura Bay in Hyogo prefecture (Table 2). Considering the follwing advantages: (1) since the present virus has an extremely strong viability, great effect is expected from small-scale and low-cost application, (2) the present virus is isolated from water in natural environment, and (3) the present virus specifically infects and kills Heterocapsa sp. it is expected that the dispersion of the present virus is effective to prevent Heterocapsa red tide.

TABLE 2

List of isolated clonal viruses

| Clonal virus | Isolation locality | Host strain |
|---|---|---|
| HcV01 | surface sea water of Wakinoura Fishing Port | Hu9433(−) |
| HcV02 | surface sea water of Wakinoura Fishing Port | Hu9433(−) |
| HcV03 | surface sea water of Wakinoura Fishing Port | HA92-1 |
| HcV04 | surface sea water of Wakinoura Fishing Port | HA92-1 |
| HcV05 | surface sea water of Wakinoura Fishing Port | HA92-1 |
| HcV06 | surface sea water of Fukuura Bay | HA92-1 |
| HcV07 | surface sea water of Fukuura Bay | HA92-1 |
| HcV08 | surface sea water of Fukuura Bay | HA92-1 |
| HcV09 | surface sea water of Fukuura Bay | HA92-1 |
| HcV10 | surface sea water of Fukuura Bay | HA92-1 |

The above clonal viruses are preserved by a study group in Red Tide Biology Section, Harmful Algal Bloom Division, National Research Institute of Fisheries and Environment of Inland Sea (The governor: Kunihiko FUKUSHO), and are ready to be subdivided under Article 27(3)of the Japanese Patent Law.

Effect of the Invention

The present invention provides a virus capable of specifically infecting and growing within a member of algae Heterocapca sp. Moreover, the present invention provides a method for isolating the virus capable of specifically infecting and growing within a member of algae Heterocapca sp. Furthermore, the present invention provides a method for subculturing the virus conserved by the method stated above. The use of the virus of the present invention can prevent red tide.

What is claimed is:

1. An isolated virus that specifically infects and grows within a member of algae Heterocapsa sp.

2. The virus according to claim 1, wherein the member of algae Heterocapsa sp. is *Heterocapsa circularisquama*.

3. The virus according to claim 2, which lacks a tail and an adventitia, adopts a sphere-like regular icosahedral structure with a particle size of approx. 0.1 to 0.2 $\mu$m, and has double-stranded DNA.

4. A method for isolating a virus that specifically infects and grows within a member of algae Heterocapsa sp. comprising:

(a) filtrating with a filter a liquid sample containing a member of Heterocapsa sp. infected with said virus;
    (b) inoculating an obtained filtrate into a culture solution of a member of algae Heterocapsa sp. and culturing; and
    (c) cloning said virus by performing a limiting dilution on a culture solution wherein said Heterocapsa sp. is lysed.

5. An agent for preventing red tide, which comprises, as an active ingredient, an isolated virus that specifically infects and grows within a member of algae Heterocapsa sp.

6. A method for preventing red tide comprising dispersing a virus that specifically infects and grows within a member of algae Heterocapsa sp. in red tide-fouled waters.

7. A method for subculturing a virus that specifically infects and grows within a member of algae Heterocapsa sp. comprising repeating at least once the steps of:

(a) centrifuging a culture solution of a member of algae Heterocapsa sp., wherein cell lysis is observed as a result of infection with said virus;
    (b) inoculating an obtained supernatant into a culture solution of a member of algae Heterocapsa sp.; and
    (c) culturing.

8. The method according to claim 7, wherein the culture is performed at a temperature of 20 to 30° C., photon density of 40 to 70 $\mu$mol photons m$^{-2}$ s$^{-1}$, and under a light-dark cycle.

* * * * *

UNITED STATES PATENT AND TRADEMARK OFFICE
CERTIFICATE OF CORRECTION

PATENT NO. : 6,544,928 B2
DATED : April 8, 2003
INVENTOR(S) : Hiraoka et al.

It is certified that error appears in the above-identified patent and that said Letters Patent is hereby corrected as shown below:

<u>Title page,</u>
Item [57], ABSTRACT,
Lines 3, 5, 7, 8, 10-11, 18, 21 and 22, "Heterocapsa" should read -- *Heterocapsa* --.

<u>Column 11,</u>
Lines 19 and 21, "Heterocapsa" should read -- *Heterocapsa* --.

<u>Column 12,</u>
Lines 2, 4 and 7, "Heterocapsa" should read -- *Heterocapsa* --; and
Lines 10, 13, 15, 18 and 21, "Heterocapsa" should read -- *Heterocapsa* --.

Signed and Sealed this

Second Day of September, 2003

JAMES E. ROGAN
*Director of the United States Patent and Trademark Office*